(12) United States Patent
Fisker et al.

(10) Patent No.: US 9,949,628 B2
(45) Date of Patent: Apr. 24, 2018

(54) ALIGNMENT OF DENTAL MODEL USING 2D PHOTOGRAPH

(71) Applicant: 3SHAPE A/S, Copenhagen K (DK)

(72) Inventors: Rune Fisker, Virum (DK); Sven Nonboe, Hillerød (DK)

(73) Assignee: 3Shape A/S, Copenhagen K (DK)

( * ) Notice: Subject to any disclaimer, the term of this patent is extended or adjusted under 35 U.S.C. 154(b) by 0 days.

(21) Appl. No.: 14/906,189

(22) PCT Filed: Jul. 17, 2014

(86) PCT No.: PCT/EP2014/065380
§ 371 (c)(1),
(2) Date: Jan. 19, 2016

(87) PCT Pub. No.: WO2015/007843
PCT Pub. Date: Jan. 22, 2015

(65) Prior Publication Data
US 2016/0157969 A1    Jun. 9, 2016

(30) Foreign Application Priority Data
Jul. 19, 2013    (DK) .................................. 2013 70411

(51) Int. Cl.
*G06K 9/00* (2006.01)
*A61B 1/24* (2006.01)
(Continued)

(52) U.S. Cl.
CPC .............. *A61B 1/24* (2013.01); *A61B 5/0077* (2013.01); *A61B 5/0088* (2013.01);
(Continued)

(58) Field of Classification Search
CPC .............. A61B 5/00; A61C 9/00; A61C 19/00
(Continued)

(56) References Cited

U.S. PATENT DOCUMENTS 7,065,243 B2 * 6/2006 Boland .............. A61C 13/0004
345/420
8,740,614 B2 * 6/2014 Wen .......................... A61C 7/00
433/24

(Continued)

FOREIGN PATENT DOCUMENTS

EP        2 159 724 A2    3/2010
WO   WO 2004/098378 A2   11/2004
(Continued)

OTHER PUBLICATIONS

D. Grest, "Marker-Free Human Motion Capture in Dynamic Cluttered Environments from a Single View-Point", PhD Thesis, 2007. (171 pages).

(Continued)

*Primary Examiner* — Abolfazl Tabatabai
(74) *Attorney, Agent, or Firm* — Buchanan Ingersoll & Rooney PC

(57) ABSTRACT

A method for setting the axis of rotation between a virtual maxillary model and a virtual mandible model to a virtual hinge axis representing the axis of rotation of the mandibular condyles includes the steps of, obtaining at least one 2D photograph of the face of a patient comprising at least one facial feature, obtaining a virtual dental model comprising the virtual maxillary model and the virtual mandible model representing at least a part of the dental situation of the patient, aligning the virtual dental model with the at least one facial feature, determining the virtual hinge axis based on the at least one 2D photograph, and setting the axis of rotation to the virtual hinge axis.

12 Claims, 3 Drawing Sheets

(51) Int. Cl.

| | | |
|---|---|---|
| | *A61C 9/00* | (2006.01) |
| | *A61C 11/02* | (2006.01) |
| | *A61B 5/00* | (2006.01) |
| | *A61C 13/00* | (2006.01) |
| | *A61C 13/34* | (2006.01) |
| | *A61C 3/00* | (2006.01) |
| | *A61C 19/045* | (2006.01) |

(52) U.S. Cl.
CPC ............ *A61C 9/0046* (2013.01); *A61C 11/02* (2013.01); *A61C 13/0004* (2013.01); *A61C 13/34* (2013.01); *A61C 19/045* (2013.01)

(58) Field of Classification Search
USPC ....... 382/128–134; 433/24, 69, 73, 213, 215
See application file for complete search history.

(56) References Cited

U.S. PATENT DOCUMENTS

| | | | |
|---|---|---|---|
| 9,508,106 | B1* | 11/2016 | Salmassy ............. A61C 8/0093 |
| 2002/0048741 | A1 | 4/2002 | Jordan et al. |
| 2008/0057466 | A1 | 3/2008 | Jordan et al. |
| 2010/0145898 | A1 | 6/2010 | Malfliet et al. |
| 2011/0045428 | A1 | 2/2011 | Boltunov et al. |
| 2013/0158958 | A1 | 6/2013 | Methot |
| 2013/0204600 | A1* | 8/2013 | Mehra ................. G06F 19/3437 703/11 |
| 2014/0313304 | A1 | 10/2014 | Adriaens |

FOREIGN PATENT DOCUMENTS

| | | |
|---|---|---|
| WO | WO 2004/098378 A3 | 11/2004 |
| WO | WO 2009/133131 A1 | 11/2009 |
| WO | WO 2012/006717 A1 | 1/2012 |
| WO | WO 2013/067606 A2 | 5/2013 |

OTHER PUBLICATIONS

International Search Report (PCT/ISA/210) dated Nov. 6, 2014, by the European Patent Office as the International Searching Authority for International Application No. PCT/EP2014/065380. (3 pages).

Written Opinion (PCT/ISA/237) dated Nov. 6, 2014, by the European Patent Office as the International Searching Authority for International Application No. PCT/EP2014/065380. (3 pages).

Danish Search Report dated Mar. 4, 2014, in the corresponding Danish Patent Application No. PA 2013 70411. (6 pages).

* cited by examiner

ALIGNMENT OF DENTAL MODEL USING 2D PHOTOGRAPH

FIELD OF THE INVENTION

This invention generally relates to relating the condylar axis of a patient to a virtual dental model representing the teeth of the patient. In particular it relates to aligning the virtual dental model in a virtual articulator in order to simulate the masticatory system of the patient and thereby enabling the dentist to provide improved treatment.

BACKGROUND OF THE INVENTION

Software for designing dental restoration is today very common and is used as an alternative or addition to manual dental technician work. Recently jaw movement simulation modules have been added to such software. In particular virtual articulators, which represent physical articulators, have been included wherein the virtual designed dental model can be placed and the jaw movement simulated in an environment familiar to the dental technician.

However, many of these simulation modules do not have any easy ways to transfer patient specific settings relevant to jaw movement, such as the placement of the hinge axis relative to the jaw or the angle of condylar guidance. Currently these are primarily set based on average values and not patient specific evaluations.

Radiographic imaging, such as x-ray, is sometimes used to determine the position of the temporal mandibular joint (TMJ) and can be used to estimate the hinge axis. However, taking an x-ray is undesirable due to radiation exposure. Moreover, due to the radiation emitted radiographic imaging is usually only concentrated around the teeth of the jaw. If the TMJ is to be included, a larger area needs to be covered and the patient is accordingly exposed to a higher radiation dose.

Moreover, since 2D x-ray images are an image of superimposed structures as photons travel through the tissue it is very difficult to determine perspective and viewing angle of the generated 2D x-ray image.

Accordingly, there exists a need for a method not involving radiographic imaging or other expensive imaging techniques that simply and effectively can obtain patient specific information which can be used to simulate jaw movement in higher detail then known hitherto.

SUMMARY

Disclosed is a method for setting the axis of rotation between a virtual maxillary model and a virtual mandible model to a virtual hinge axis representing the axis of rotation of the mandibular condyles, the method comprises the steps of:
  obtaining at least one 2D photograph of the face of a patient comprising at least one facial feature,
  obtaining a virtual dental model comprising the virtual maxillary model and the virtual mandible model representing at least a part of the dental situation of the patient,
  aligning the virtual dental model with the at least one facial feature,
  determining the virtual hinge axis based on the at least one 2D photograph, and
  setting the axis of rotation to the virtual hinge axis.
  Accordingly, the virtual dental model may be correctly aligned with the hinge axis of the patient. This allows for improved digital simulation of the masticatory system of the patient and improved treatment options for the patient.

Different embodiment will in the following be described in relations to a general overview of some of the problems encountered as shown in the chart in FIG. 1.

The embodiment may overlap some of the steps and particularly it should be understood that they are not exclusive, i.e. the different embodiments may be used in combination. Furthermore, not all the parts shown in FIG. 1 needs necessarily be executed since for some applications only certain requirements are needed as will be understood.

Within the present application a photograph should be understood as being an image obtained by recording visible light, i.e. wavelengths from about 390 to 700 nm. Accordingly, a photograph should not be understood as being a radiographic image or a magnetic resonance image (MRI).

A photograph can be obtained using analogue well known techniques or digital well known techniques. The photograph can be post-processed in order to e.g. clarify or emphasize specific features or landmarks.

Moreover, when referring to an entity being 'virtual', e.g. virtual dental model or virtual articulator, the term virtual refers to a digital representation of a physical entity. Accordingly, unless otherwise stated the term 'virtual' may be replaced by the term 'digital' or 'digital representation of'.
Correcting for Perspective/Estimating Field of View One issue which should be considered when aligning the 2D photograph and the virtual dental model and possibly also the virtual articulator if applied in order to obtain improved precision when aligning is the perspective in which the 2D photograph was taken.

In general terms it can be said that the perspective influences our 2D photograph in two ways. Perspective makes objects that was close to the camera appear bigger than object further away and perspective makes objects that extends along the line of sight, ie. towards the vanishing point, appear shorter than objects that extend across the line of sight.

The perspective which is determined by the field of view or angle of view is a concept which is well known within the field of optics.

Thus, if we want to correctly align the 2D photograph and the virtual dental model we must either align the two using the same perspective, ie. with the same field of view or eliminate the perspective factor.

In one embodiment a calibration device is used when the 2D photograph is taken. The calibration device has a known size and shape and is placed on the patient so that it is visible in the final 2D photograph. Thus, by knowing the size and shape of the calibration device the field of view from which the 2D photograph was taken can be determined. When the field of view is known the virtual dental model can be aligned to the same field of view and the 2D photograph can be aligned to the dental model.

In another embodiment the camera used to take the 2D photograph is using a telecentric lens. A telecentric lens is designed so that they produce a orthographic view of the subject. This eliminates the perspective factor and the 2D photograph may be aligned without need to take the field of view into account. However, a telecentric lens is expensive and requires special camera bodies. In addition the lens only captures a relative small area of the view and thus it might be necessary to take several photographs and stich them together to get the full 2D photograph.

In alternative embodiment the perspective factor may be minimized or made negligible by using a zoom lens. By fully zooming in and moving back so that the subject is within the cameras frame a 2D photograph may be obtained wherein the effect of the perspective from the field of view can be made negligible when aligning the 2D photograph to the virtual dental model. The effect of this embodiment improves the higher the zoom level used.

In yet another embodiment the photographer records different parameters which are used for estimating the field of view of the camera. Such parameters can for example be distance to the subject and/or the zoom level. Some of these parameters may even be recorded by the camera in the metadata tags in Exif data for the 2D photograph.

The above embodiments all describes ways to take into account the perspective factor when taking the 2D photograph. However, in many situations this may not be desirable since it requires that the photographer uses specific equipment or remembers to take the 2D photograph at specific settings and/or record relevant parameters for later use.

Accordingly it is an advantage if the evaluation of the field of view, and thereby the perspective, is post-processed digitally in a computer after the 2D photograph has been taken.

In one embodiment where the 2D photograph is aligned to the virtual dental model in a virtual environment, e.g. in a design software program executed on a computer, at least four alignment points on the 2D photograph and corresponding four alignment points are identified on the virtual dental model. The alignment points are used to align the 2D photograph to the virtual dental mode. The alignment points will typically be facial features identified in the 2D photograph and where corresponding points are identified in the virtual dental model. Such facial features can for example be visible teeth in the 2D photograph, where corresponding teeth in the virtual dental model are identified.

Aligning 2D Photograph to the Virtual Dental Model

With the field of view determined, or the perspective factor eliminated or minimized the 2D photograph and the virtual dental model and alternatively the virtual articulator can be aligned correctly.

In one embodiment the virtual dental model is derived from a 3D scan of the patient's dentition, for example from an intra-oral scan, scan of a dental impression or a gypsum model. In such cases the dimensions of the virtual dental model corresponds to the original and thus by scaling the 2D photograph to fit the virtual dental model the 2D photograph will be scaled accordingly.

The final alignment can in one embodiment be done by identifying facial features in the 2D photograph with corresponding point in the virtual dental model. For example, if the 2D photograph shows visible teeth, these forms facial features which can be identified in the virtual dental model and thus alignment can be provided.

When the 2D photograph has been aligned to the virtual dental model the hinge axis can be determined.

In one embodiment this is done manually by the user identifying the hinge axis as a point in the 2D photograph. If the 2D photograph is a profile picture of the patient the hinge axis is then simply set as an axis perpendicular to the 2D photograph. However, if the 2D photograph is a picture of the patient from another angle more information is needed to determine the orientation of the hinge axis. This can for example be done manually by the user or the software can give a best guess, for example based on the virtual dental model which can be used as reference since it is aligned to the 2D photograph.

Accordingly, it can be understood that different types and number of 2D photograph s can be used for different purposes. E.g. in one embodiment the 2D photograph shows the patient from the side in profile. In another embodiment at least two photographs s are obtained of the patient from different angles, for example a first 2D photograph from the side and a second 2D photograph from the front. In yet another embodiment photographs are taken perpendicular on known planes such as the mid-plane/the sagittal plane or the coronal plane.

In one embodiment the 2D shows the patient with the mouth closed in static occlusion.

With the hinge axis determined the upper and lower jaw of the virtual dental model will simulate the patients opening and closing around the hinge axis.

Thus, in one embodiment a simple simulation of the jaw movement may be performed around the hinge axis.

Aligning the Virtual Dental Model and the Virtual Articulator

In one embodiment a virtual articulator is aligned with the 2D photograph and the virtual dental model. This is advantageously where the dentist or dental technician wants to simulate a physical articulator setup. Accordingly, the virtual articulator simulates a corresponding physical articulator. This lets the user test the setup in an environment he is used to.

In one embodiment the virtual articulator and the 2D photograph are aligned using a common reference plane. The hinge axis, which is also represented in an articulator, defines the first reference. Accordingly, it is only necessary to define a third point which is present on both the 2D photograph and the virtual articulator in order to have a common reference plane which may be used for alignment.

In most physical articulators the upper member extends along a known plane, or have features which are used to define such a plane. Such plane is typically defined by the hinges axis, represented by the condylar joints in the articulator and a third point on the upper member of the articulator. This point is commonly repersenting either the orbitale (the lowest anterior point on the lower margin of the orbit) or the acanthion (tip of the anterior nasal spine). The plane defined by the hinge axis and the orbitale represent the Frankfurt/Frankfort plane and the plane defined by the hinge axis and acanthion represent the Camper plane. These planes are both well known to the dentist and dental technician and thus easy to define. However, other planes could be used as long as they can be derived from both the articulator and the 2D photograph.

Accordingly, in one embodiment the method further comprises arranging the virtual dental model in a virtual articulator simulating a corresponding physical articulator comprising the steps of:

defining an alignment reference plane in the 2D photograph, arranging the virtual dental model in the virtual articulator by aligning the articulator alignment plane with a corresponding alignment reference plane in the virtual articulator.

With the common reference plane identified in the 2D photograph and in the virtual articulator they can be aligned correctly and with the 2D photograph aligned to the virtual dental model no scaling is necessary since the virtual articulator is a virtual representation of a physical articulator and thus the dimension of the physical articulator is also transferred to the virtual articulator.

The above describes how the virtual articulator is aligned to the 2D photograph and thus also to the virtual dental model. However, this only aligns the parts in one plane and an additional step is necessary to completely align the virtual dental model and the virtual articulator in space.

In one embodiment this alignment in space of the virtual articulator and the virtual dental model is accomplished by using a second 2D photograph taken from another field of view.

In another embodiment alignment in space can be done by aligning the virtual dental model and the virtual articulator along some estimated values. For example in one embodiment a plane representing the median plane is defined by the user or estimated by the computer in the virtual dental model and this is aligned to a mid-plane in the virtual articulator dividing the virtual articulator in a left and a right part.

The above describes how the virtual dental model is aligned to the hinge axis, which is required as a minimum to be able to simulate jaw movement.

However, the temporal mandibular joint (TMJ) does not only work a hinge movement but also allow for backward and forward translation as the condyle is allowed to slide along the glenoid fossa.

This movement is referred to as the condylar guidance and the angle thereof can be set in most articulators.

One way to do this is to simply set the angle to an average value, which is often done when using the physical articulator.

Accordingly, in one embodiment where the virtual articulator has been aligned to the 2D photograph by using a reference plane representing the Frankfurt plane the average value is 40°. If the reference plane represents the Camper plane the average value is 30°.

Thus, in one embodiment this alignment can be used to simulate jaw movement using average condylar guidance.
Determining Condylar Guidance However, it is of course preferred that the actual angle for condylar guidance in the virtual articulator for the specific patient is determined.

In practice this is done by taking a so-called protrusive record. This is a bite record where the patient bites into an impression material while protruding the lower jaw.

The protrusive record is then used in the articulator setup, where the dental model has been placed in the articulator by using a facebow transfer. The control for condylar guidance is loosened allowing it to move, then the maxilla and mandible are placed so that they fit the protrusive record. When this is done the control for condylar guidance is tightened and the condylar guidance can be read of the control. In one embodiment this reading can of course be transferred to the virtual articulator. However, this has the disadvantage that a physical articulator setup has to be done.

In one embodiment the condylar guidance angle may be determined virtually by taking a protrusive 2D photograph, showing the patient protruding the mandible. Preferably this protrusive 2D photograph shows some of the teeth, preferably teeth placed both in the maxilla and in the mandible.

By aligning the virtual dental model to the protrusive 2D photograph after the virtual dental model has been aligned to the first 2D photograph the angle of the condylar guidance may be derived by considering the shift of the virtual mandible as it moves between the position in the first 2D photograph and the position in the protrusive 2D photograph relative to the reference plane.

Furthermore, the invention relates to a computer program product comprising program code means for causing a data processing system to perform the method according to any of the embodiments, when said program code means are executed on the data processing system, and a computer program product, comprising a computer-readable medium having stored there on the program code means.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

Figure 1:
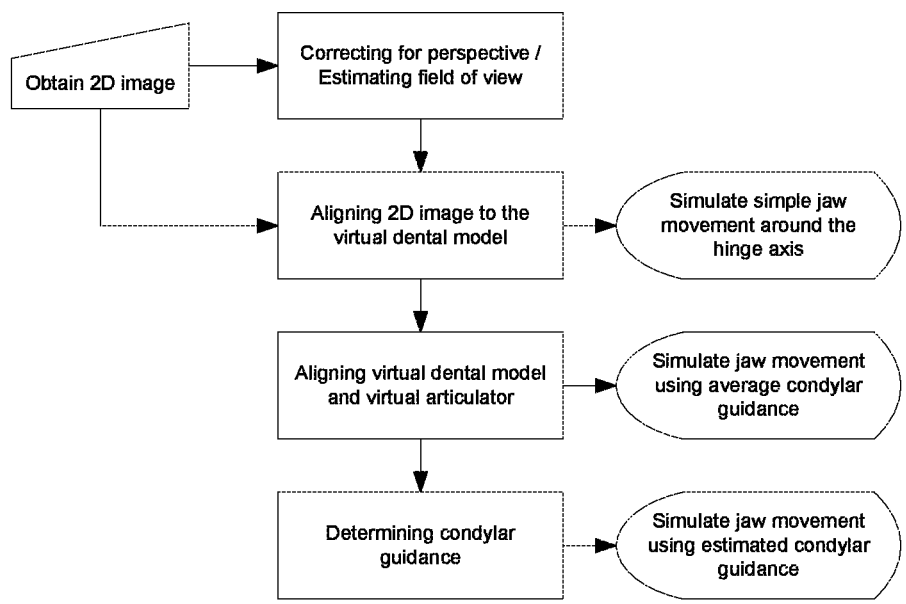
FIG. 1 is a chart giving a general overview of some of the problems encountered.

In the following description, reference is made to the accompanying figures, which show by way of illustration how the invention may be practiced.

A method for aligning the virtual dental model, the 2D photograph and the virtual articulator as disclosed herein will in the following be described with reference to FIGS. 2a-2e.

A virtual dental model 1 is obtained comprising a virtual maxilla 2 and a virtual mandible 3, representing the dentition of a specific patient 4. The virtual dental model has been formed from an intra-oral scan of the patient, for example by using the TRIOS handheld scanner manufactured by 3Shape A/S, Denmark. Other scanning methods could be used as is known in the art.

A 2D photograph 5 of a patient 4 seen in profile is obtained by taking a photo using a digital camera and subsequently loading the 2D photograph into the same software as the virtual dental model. The 2D photograph shows the patient smiling while keeping her jaw in static occlusion, i.e. the mouth is closed in natural position. Thus the teeth can be seen in a known reference position. If the patient did not have a smile that shows the teeth the dentist would ask her to pull her lips back before taking the photo.

With the virtual dental model 1 and the 2D photograph 5 in the virtual environment the user identifies four reference points 6a, 6b, 6c and 6d in the virtual dental model 1 and corresponding four reference point 6a', 6b', 6c' and 6d' in the 2d photograph.

Figure 2:
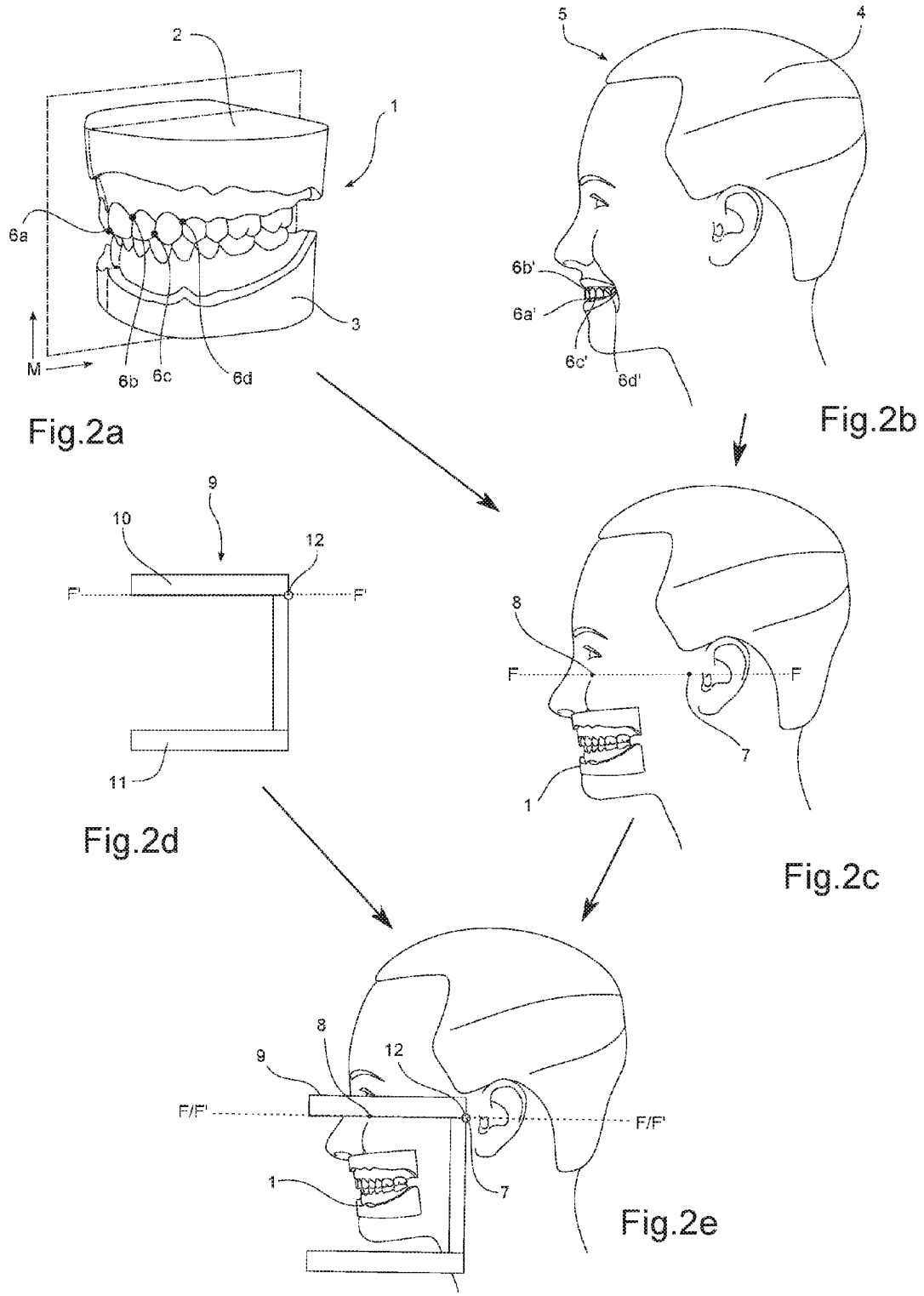
FIG. 2 shows a work flow of a method of aligning a virtual dental model and a virtual articulator using a 2D photograph as described herein.

With the four reference points identified the software is able to estimate the camera position and filed of view used when the 2D photograph was taken. These parameters may then be transferred to the view of the virtual dental model, so that the 2D photograph and the virtual dental model are viewed from the same camera position and field of view and thus are aligned. The principles hereof are for example described in "Marker-Free Human Motion Capture: Estimation Concepts and Possibilities with Computer Vision Techniques from a Single Camera View Point" by Daniel Grest, published by LAP LAMBERT Academic Publishing (Jul. 22, 2010), ISBM-13:978-3838382227. The final alignment as shown in FIG. 2c shows the virtual dental model 1 aligned on top of the 2D photograph 5 of the patient 4.

With the alignment of the 2D photograph and the virtual dental model complete the user identifies the location of the hinge axis of the temporal mandibular joint (TMJ) by hinge point 7 on the 2D photograph.

Since the 2D photograph is a profile picture the software estimates the hinge axis to be perpendicular to the hinge point. Thus, the hinge axis is determined and a simple simulation of the jaw movement can be done by rotating the maxilla and mandible of the virtual dental model relative to each other around the hinge axis.

However, even more advanced simulation can be done by providing a reference plane for e.g. condylar guidance. Different reference planes can be used, such as the Frankfurt plane or the Camper plane. For the current application there is not one which is necessarily better than another, however, it should be possible to place the plane in the 2D photograph. Thus, for example, the Frankfurt plane F-F can be determined by using the hinge point 7 and the orbitale 8 as references.

In addition the reference plane aids in aligning a virtual articulator 9 if the user so desires.

The virtual articulator 9 shown in FIG. 2*d* represents a similar physical articulator and comprises an upper member 10 which is rotatable mounted to a lower member 11 around an axis 12. The axis 12 represents the hinge axis of the TMJ.

The upper member 10 extends along the plane F'-F' which corresponds to the Frankfurt plane F-F in the 2D photograph. Accordingly the virtual articulator can be aligned in 2D photograph by using the Frankfurt plane and the hinge axis as references.

With the virtual articulator and the virtual dental model aligned in a plane perpendicular to the hinge axis it remains to align the virtual articulator and the virtual dental along the hinge axis in order to get proper alignment in space.

Figure 3:
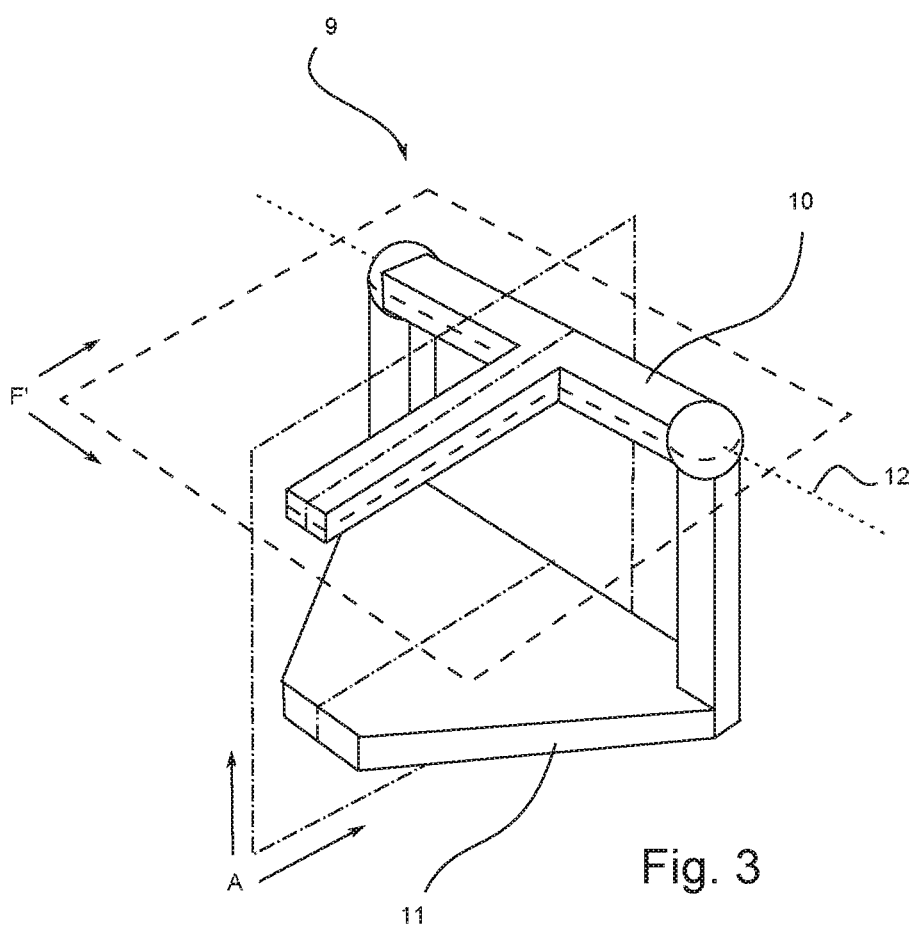
FIG. 3 shows planes relative to a virtual articulator.

This is done by defining a medial plane M-M in the virtual dental model and aligning this with a mid-plane A-A in the virtual articulator as shown in FIG. 3. In order to facilitate alignment movement can be limited so that movement is only limited in one plane at the time, e.g. while alignment is performed between the medial plane M-M and the mid-plane A-A movement in the Frankfurt plane F'/F-F'/F is locked.

With the virtual dental model and the virtual articulator correctly aligned it is possible to simulate jaw movement using the articulator settings.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. A method for setting the axis of rotation between a virtual maxillary model and a virtual mandible model to a virtual hinge axis representing the axis of rotation of the mandibular condyles, the method comprises the steps of:
   obtaining at least one 2D photograph of the face of a patient comprising at least one facial feature,
   obtaining a virtual dental model comprising the virtual maxillary model and the virtual mandible model representing at least a part of the dental situation of the patient,
   aligning the virtual dental model with the at least one facial feature,
   determining the virtual hinge axis based on the at least one 2D photograph, and
   setting the axis of rotation to the virtual hinge axis,
   wherein the at least one 2D photograph is a photograph taken with a 2D camera of an external view of the patient.

2. A method according to claim 1, wherein the method further comprises arranging the virtual dental model in a virtual articulator simulating a corresponding physical articulator comprising the steps of:
   defining an alignment reference plane in the 2D photograph,
   arranging the virtual dental model in the virtual articulator by aligning the articulator alignment plane with a corresponding alignment reference plane in the virtual articulator.

3. A method according to claim 2, wherein the reference alignment plane in the 2D photograph is the Frankfurt plane.

4. A method according to claim 1, wherein the 2D photograph is scaled to the virtual dental model.

5. A method according to claim 1, wherein the 2D photograph shows the patient from the side.

6. A method according to claim 1, wherein at least two 2D photograph s are obtained of the patient from different angles.

7. A method according to claim 6, wherein a first 2D photograph is from the side and a second 2D photograph is from the front.

8. A method according to claim 1, wherein the at least one 2D photograph shows the jaws in static occlusion.

9. A method according to claim 8, wherein an angle of condylar guidance is determined by the shift of the virtual mandible model relative to the virtual maxillary model between the static occlusion and the protruded position.

10. A method according to claim 1, wherein the at least one 2D photograph shows the mandible in a protruded position.

11. A method for setting the axis of rotation between a virtual maxillary model and a virtual mandible model to a virtual hinge axis representing the axis of rotation of the mandibular condyles, the method comprises the steps of:
    obtaining at least one 2D photograph of the face of a patient comprising at least one facial feature,
    obtaining a virtual dental model comprising the virtual maxillary model and the virtual mandible model representing at least a part of the dental situation of the patient,
    aligning the virtual dental model with the at least one facial feature,
    determining the virtual hinge axis based on the at least one 2D photograph, and
    setting the axis of rotation to the virtual hinge axis,
    wherein the at least one 2D photograph is a photograph taken with a 2D camera of a side, profile view of the patient.

12. A method for setting the axis of rotation between a virtual maxillary model and a virtual mandible model to a virtual hinge axis representing the axis of rotation of the mandibular condyles, the method comprises the steps of:

obtaining at least one 2D photograph of the face of a patient comprising at least one facial feature, obtaining a virtual dental model comprising the virtual maxillary model and the virtual mandible model representing at least a part of the dental situation of the patient, aligning the virtual dental model with the at least one facial feature, determining the virtual hinge axis based on the at least one 2D photograph, and setting the axis of rotation to the virtual hinge axis, wherein the virtual dental model is aligned with the at least one facial feature in the 2D photograph.

* * * * *